United States Patent
Wagenaar Cacciola et al.

(10) Patent No.: US 10,384,076 B2
(45) Date of Patent: Aug. 20, 2019

(54) FLEXIBLE LIGHT THERAPY DEVICE, A PLASTER AND A BANDAGE

(75) Inventors: Giovanna Wagenaar Cacciola, Eindhoven (NL); Elvira Johanna Maria Paulussen, Reppel-Bocholt (BE); Jorgen Meeusen, Eindhoven (NL); Gregorius Wilhelmus Maria Kok, Veldhoven (NL); Georges Marie Calon, Eindhoven (NL); Guofu Zhuo, Best (NL); Liesbeth Van Pieterson, Heeze (NL); Claudia Mutter, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 179 days.

(21) Appl. No.: 13/816,937

(22) PCT Filed: Aug. 9, 2011

(86) PCT No.: PCT/IB2011/053546
§ 371 (c)(1),
(2), (4) Date: Feb. 14, 2013

(87) PCT Pub. No.: WO2012/023086
PCT Pub. Date: Feb. 23, 2012

(65) Prior Publication Data
US 2013/0144364 A1    Jun. 6, 2013

(30) Foreign Application Priority Data

Aug. 17, 2010  (EP) .................................. 10173005
Nov. 19, 2010  (EP) .................................. 10191821

(51) Int. Cl.
*A61N 5/06*     (2006.01)
*A61N 5/00*     (2006.01)

(52) U.S. Cl.
CPC ......... *A61N 5/0625* (2013.01); *A61N 5/0613* (2013.01); *A61N 5/0616* (2013.01);
(Continued)

(58) Field of Classification Search
CPC .............................................. A61N 2005/0645
(Continued)

(56) References Cited

U.S. PATENT DOCUMENTS 4,983,851 A * 1/1991 Masuda et al. ............ 250/493.1
5,358,503 A * 10/1994 Bertwell et al. ................ 606/27
(Continued)

FOREIGN PATENT DOCUMENTS

CN    201182843 Y    1/2009
EP       1074275 A1    2/2001
(Continued)

OTHER PUBLICATIONS

Nakamura et al, "Regional Differences in Temperature Sensation and Thermal Comfort in Humnas", J. Appl. Physiol., vol. 105, 2008, pp. 1897-1906.
(Continued)

*Primary Examiner* — Carl H Layno
*Assistant Examiner* — Manolis Pahakis

(57) ABSTRACT

A flexible light therapy device, a bandage and a plaster for providing a therapeutic effect to a treatment target area (226) of a living being are provided. The flexible light therapy device comprises a light source (214) for emitting light (220), a light transmitting element (212) and a heat management means (210). The light transmitting element (212) is of a flexible light transmitting material and is optically coupled to the light source (214). The light transmitting element (212) comprises a light exit window (222) to emit the light (220) towards the treatment target area (226). The heat management means (210) is thermally coupled to the
(Continued)

treatment target area (226) and distributes heat and controls the distribution of heat across the treatment target area (226). Part of the distributed heat may originate from the light source (214).

6 Claims, 10 Drawing Sheets

(52) U.S. Cl.
CPC .. *A61N 2005/005* (2013.01); *A61N 2005/063* (2013.01); *A61N 2005/0645* (2013.01); *A61N 2005/0652* (2013.01); *A61N 2005/0653* (2013.01); *A61N 2005/0663* (2013.01)

(58) Field of Classification Search
USPC ..................................... 606/1–19; 607/88–94
See application file for complete search history.

(56) References Cited

U.S. PATENT DOCUMENTS

| | | | |
|---|---|---|---|
| 5,616,140 A | 4/1997 | Prescott | |
| 5,876,107 A | 3/1999 | Parker et al. | |
| 6,290,713 B1* | 9/2001 | Russell | 607/88 |
| 6,443,978 B1 | 9/2002 | Zharov | |
| 6,569,189 B1* | 5/2003 | Augustine et al. | 607/96 |
| 6,991,644 B2* | 1/2006 | Spooner | A61N 5/0614 |
| | | | 128/898 |
| 7,077,840 B2* | 7/2006 | Altshuler | A61B 18/203 |
| | | | 606/2 |
| 7,351,252 B2 | 4/2008 | Altshuler et al. | |
| 7,452,356 B2* | 11/2008 | Grove et al. | 606/9 |
| 8,996,131 B1* | 3/2015 | Owen | A61N 1/05 |
| | | | 607/116 |
| 2001/0046652 A1* | 11/2001 | Ostler | A61C 19/004 |
| | | | 433/29 |
| 2003/0167080 A1* | 9/2003 | Hart et al. | 607/88 |
| 2003/0195494 A1* | 10/2003 | Altshuler et al. | 606/9 |
| 2003/0233138 A1* | 12/2003 | Spooner | A61B 18/203 |
| | | | 607/93 |
| 2004/0059399 A1 | 3/2004 | Neuberger | |
| 2004/0147984 A1* | 7/2004 | Altshuler et al. | 607/88 |
| 2005/0177093 A1* | 8/2005 | Barry et al. | 604/20 |
| 2005/0237739 A1* | 10/2005 | Lee | A61N 5/0613 |
| | | | 362/241 |
| 2005/0256554 A1 | 11/2005 | Malak | |
| 2007/0049998 A1* | 3/2007 | Conrad | A61F 7/007 |
| | | | 607/96 |
| 2007/0083139 A1 | 4/2007 | Tsuruda et al. | |
| 2007/0208395 A1* | 9/2007 | Leclerc et al. | 607/86 |
| 2007/0233208 A1 | 10/2007 | Kurtz et al. | |
| 2007/0239232 A1 | 10/2007 | Kurtz et al. | |
| 2008/0172045 A1* | 7/2008 | Shanks | A61N 5/0616 |
| | | | 606/3 |
| 2008/0269849 A1 | 10/2008 | Lewis | |
| 2009/0088824 A1* | 4/2009 | Baird et al. | 607/90 |
| 2009/0198173 A1* | 8/2009 | Samuel et al. | 604/20 |
| 2009/0299419 A1* | 12/2009 | West | 607/3 |
| 2010/0049177 A1* | 2/2010 | Boone, III | A61H 9/0057 |
| | | | 606/9 |
| 2010/0145321 A1* | 6/2010 | Altshuler | A61B 18/203 |
| | | | 606/9 |
| 2011/0022132 A1* | 1/2011 | Kim | A61H 7/006 |
| | | | 607/91 |
| 2012/0035690 A1* | 2/2012 | Turtzo | 607/90 |
| 2012/0116373 A1* | 5/2012 | Moench | A61B 18/203 |
| | | | 606/9 |
| 2015/0051671 A1* | 2/2015 | Browne | A61N 5/0616 |
| | | | 607/90 |

FOREIGN PATENT DOCUMENTS

| | | |
|---|---|---|
| JP | 62270679 A | 11/1987 |
| KR | 2006089361 A | 8/2006 |
| WO | 2001014012 A1 | 3/2001 |
| WO | 2003070315 A2 | 8/2003 |
| WO | 2005046793 A2 | 5/2005 |
| WO | 2008017975 A1 | 2/2008 |

OTHER PUBLICATIONS

Delayed Onset Muscle Soreness, Wikipedia, Downloaded From http://en.wikipedia.org/wiki/delayed_onset_muscle_soreness on May 24, 2016, 5 Pages.
Synovial Fluid, Wikipedia Downloaded From http://en.wikipedia.org/wiki/synovial_fluid on May 24, 2016, 4 Pages.
Richeimer, Fibromyalgia, The Richeimer Pain Institute, Nov. 2000, pp. 1-3.
Hallenbeck, "Types of Pain", Palliative Care Perspectives, Chapter 4, Pain Management, 2003, Downloaded From http://www.mywhatever.com/cifwriter/library/70/4922.html on May 24, 2016.

* cited by examiner

FLEXIBLE LIGHT THERAPY DEVICE, A PLASTER AND A BANDAGE

FIELD OF THE INVENTION

The invention relates to flexible light therapy devices. The flexible light therapy devices may be implemented in a plaster or a bandage which may be attached to the skin of a person or an animal and/or may be wrapped around a body portion of a person or an animal.

Flexible light therapy devices comprise a light source generating light that impinges on the skin of a treated person or animal and, depending on the color of the light, penetrates to a specific depth into the tissues below the skin surface. When the penetrated light is absorbed in the tissue, the tissue warms up. The warming up of tissues in and underlying the skin is experienced as well-being and has a therapeutic effect as well, especially pain relief. The benefits of the heat are based on a vasodilatory response in the skin which locally enhances the blood circulation. This results in a higher metabolic rate and transport of metabolites and other essential biochemical compounds. The penetration of the light to deeper tissues provides a gentle and pleasant warming effect. Further, specific wavelengths of light have an influence on the biochemical processes in the cells of the skin and underlying tissue and the flexible light therapy device may be used to slow down disadvantageous biochemical processes or stimulate beneficial biochemical processes.

BACKGROUND OF THE INVENTION

Published patent application WO01/14012A1 discloses a flexible illuminator for external phototherapy. The flexible illuminator has at least one light generating source on a flexible substrate. The flexible illuminator further has a structure for diffusing light of the at least one light generating source and has a system for transferring heat away from a skin contact surface. In the discussed embodiments a plurality of light generating sources are provided. The back side of the flexible illuminator, which is, in use, a side of the flexible illuminator facing away from the skin of the treated person, provides a heat sink for absorbing the heat generated by the plurality of light generating sources. The heat sink works together with a heat barrier between the light sources and the skin to prevent that the skin contact surface is heated to a dangerous temperature by the heat of the light generating sources. Heat is transferred in a direction away from the person who is treated with the flexible illuminator.

The flexible illuminator of the cited art only comprises heat transferring means which transfers the heat of the light sources in a direction away from the treated person or animal. However, the contact area between the flexible illuminator and the skin of the treated person or animal may still become locally too hot or remain locally too cold. So-called hot and cold spots are inconvenient for the treated person or animal and may have a negative influence on the therapeutic effect of the flexible illuminator.

SUMMARY OF THE INVENTION

It is an object of the invention to provide a flexible light therapy device which controls heat more accurately at the interface between the flexible light therapy device and the skin of a treated person or animal.

A first aspect of the invention provides a flexible light therapy device as claimed in claim 1. A second aspect of the invention provides a plaster or a bandage as claimed in claim 15. Advantageous embodiments are defined in the dependent claims.

A flexible light therapy device in accordance with the first aspect of the invention comprises a light source, a light transmitting element and a heat management means. The flexible light therapy device provides in use a therapeutic light effect to a treatment target area of a living being. The light source is for emitting light. The light transmitting element may be a flexible light transmitting material which is optically coupled to the light source such as a flexible light guide material optically coupled to the light source in a so-called side-lit configuration or may comprise a light transmitting cavity optically coupled to the light source in a so-called directOlit configuration. The light transmitting element comprises a light exit window towards the treatment target area. The heat management means is thermally coupled to the treatment target area to distribute heat and control the heat distribution across the treatment target area. The heat may originate from the treatment target area itself, but a majority of the distributed heat will originate from the light source.

The heat management means provides the effect of controlling the heat distribution across the treatment target area because the heat management means is thermally coupled to the treatment target area and in a preferred embodiment is also thermally coupled to the light source. Heat of the light source is conducted to the treatment target area. Via conduction more heat can be transferred to potentially colder area of the treatment target area and less heat can be transferred to potentially hotter areas of the treatment target area. Further, the heat management means is capable of distributing heat and thus it may transfer heat from warmer areas to colder areas, which prevents hot and cold spots at the treatment target area and therefore a strong temperature gradient across the treatment target area is prevented. Thus, the heat management means reduces temperature differences at the treatment target area, in other words, the heat distribution across the treatment target area becomes more uniform.

The inventors have realized that the therapeutic effect of the flexible light therapy device increases when, in addition to receiving light which mainly heats up the deeper tissues of the skin, the treatment target area receives heat from the light source as the result of the distribution of heat via conduction towards the treatment target area. The conducted heat is received by the top layer of the skin of the treated person or the animal, and may be conducted further to the deeper tissues of the skin. Light transfers energy via electromagnetic waves. The electromagnetic waves penetrate to a large extent directly towards the deeper tissues of the skin to warm up the deeper tissues. Thus, the flexible light therapy device provides, in use, an effective warming up of deeper tissues of the skin with radiated light and a comfortable warming up of the top layers of the skin with conducted heat.

Advantageously, energy is saved. At least a part of the residual heat of the light source is used efficiently for obtaining a therapeutic effect instead of transferring all the residual heat outside of the flexible light therapy device to the ambient environment. Thus, the light source may operate at a lower power level while the therapeutic effect is still the same.

The light transmitting element is of a flexible light transmitting material. The flexibility is high enough to allow the bending of the flexible light therapy device such that an effective emission of light towards the treatment target area is obtained. In an advantageous embodiment also an effective thermal coupling to the treatment target area may be obtained with the light transmitting element. The term 'light transmitting' means that light which is received from the light source is at least partially transmitted towards the light exit window. Thus, the light transmitting material may be transparent or translucent, and may be partially transparent or partially translucent.

It is to be noted that the flexible light transmitting material is not necessarily limited to a single material or only limited to solid materials. A combination of a solid material and gas may be used as well, or a combination of a solid material and a fluid. For example, a flexible foam material may be used to obtain a substantially fixed shape which has still the flexibility of bending the material, and cavities in the flexible foam may be filled with a light transmitting gas, which is for example air.

In another embodiment, the light therapy device comprises a plurality of light sources being optically coupled to the light transmitting element.

In an embodiment, the heat management means is thermally coupled to the light transmitting element and the light exit window is, in use, brought in contact with the treatment target area. A thermal coupling between the heat management means and the treatment target area may therefore be obtained via the light transmitting element. The light transmitting element has a specific heat conductivity and a specific heat capacity and as such the light transmitting element may assist the heat management means in distributing the heat towards the treatment target area. The light transmitting element is thus preferably not a thermal insulator. As discussed in other embodiments, the light transmitting element may have a relatively low thermal conductivity when heat conductive channels are used.

The embodiment wherein the light transmitting element has a specific heat conductivity and a specific heat capacity is especially advantageous when pulsed light emitters are used which alternate between an on and off state. The skin receives the electromagnetic waves of the light in pulses and is therefore not heated continuously. The light transmitting element, which has a specific heat capacity, temporarily stores a part of the residual heat of the light source and gradually provides at least a part of the stored heat via conduction to the skin of the treated person or animal. Thus, the skin is also warmed up in between the pulses. This provides more comfort and a beneficial therapeutic effect, while saving power during the off periods of the light source.

In another embodiment, the heat management means comprises a heat conductive layer applied to a part of a surface of the light transmitting element.

Providing a heat conductive layer at a part of the surface of the light transmitting element is an effective way of distributing heat in space and thus obtaining a heat distribution across the treatment target area which is more uniform. It is to be noted that the heat conductive layer is thermally coupled to the light transmitting element because the heat conductive layer is applied to a surface of the light transmitting element. As such the heat conductive layer assists in distributing the heat of the light source across the body of the light transmitting element, and thus the temperature differences in the light transmitting element are reduced. Consequently, the light exit window of the light transmitting element obtains a more uniform temperature distribution. If the light exit window then is brought in contact with the treatment target area, the heat distribution across the treatment target area become more uniform as well. In addition to reducing the number of cold and hot spots at the light exit window, cold and hot spots are also prevented at other areas of the light transmitting element, especially at the region where the heat conductive layer is provided. Therefore, other surfaces of the flexible light therapy device, which are not in contact with the treatment target area of a person or animal, but which are, for example, in contact with for example the clothes of the person, do not create hot spots with a temperature above a safe temperature.

The heat conductive layer may be opaque. If the heat conductive layer is opaque, the part of the surface of the light transmitting element to which the heat conductive layer is applied is preferably not the light exit window. The heat conductive layer may be provided to the light exit window. However, then it has to be at least partially light transmitting to allow at least a part of the light, which is emitted from the light exit window, to reach the treatment target area. Such a light transmitting heat conductive layer may be a layer of silicon which contains metal particles, or, in another example, the light transmitting heat conductive layer may be a structure of woven copper wires with open spaces between the copper wires. In another embodiment, if the heat conductive layer is applied to the side of the light transmitting element comprising the light exit window, and if the heat conductive layer is not light transmitting, at least a substantial part of the light exit window may not be covered by the heat conductive layer.

In an embodiment, the part of the surface of the light transmitting element to which the heat conductive layer is applied is located substantially opposite the light exit window.

In an embodiment, the heat management means is thermally coupled to the light source for receiving heat of the light source and for distributing the heat of the light source towards the treatment target area.

The heat management means absorbs the residual heat of the light source and provides at least a part of the heat to the treatment target area. Thus, the received residual heat is used to raise the temperature of the treatment target area. As such the heat transfer to the skin of the person or the animal via heat conduction is increased and a better therapeutic effect is obtained. The heat management means distributes the heat and therefore prevents that the light transmitting element becomes at a side, which is the side where the light source is coupled to the light transmitting element, relatively warm, while another side of the light transmitting element remains relatively cold. A more uniform heat distribution is obtained throughout the light transmitting element. Further, energy is saved, because the skin of the person or the animal is heated via light of the light source and via conducted residual heat from the light source and, thus, the light source may emit less light.

In another embodiment, the heat management means comprises heat conductive channels in the light transmitting element. An end of the heat conductive channels is arranged to be brought in contact with the treatment target area when the flexible light therapy device is in use. Thus, the heat conductive channels are an effective solution for distributing heat such that the heat distribution across the treatment target area becomes more uniform. Another end of the heat conductive channels may be thermally coupled to the light transmitting element. Consequently, the heat conductive channels are effective means to distribute heat from a first location towards other locations and are also effective in reducing the temperature differences within the light transmitting element, and, thus, assist in obtaining a better heat distribution at the light exit window which may also be in contact with the treatment target area. A better heat distribution across the light exit window contributes to a better heat distribution across the treatment target area. The light transmitting element has often a relatively low heat conductivity and/or a low heat capacity and thus the heat conductive channels provide a better heat conduction than the light transmitting element may provide.

It is to be noted that, if the heat conductive channels are not thermally coupled to the light transmitting element, the heat conductive channels mainly have the function of heat transport towards the treatment target area. If the heat conductive channels are also thermally coupled to the light transmitting element, the heat conductive channels also provide the function of distributing heat to the light transmitting element, and as such an additional heat transport path via the light transmitting element towards the treatment target area becomes available. It is further to be noted that "bringing the end of the heat conductive channels in contact with the treatment target area" has the meaning of "the end of the heat conductive channel is thermally coupled to the treatment target area", which actually means that another thin layer of a heat conductive material may be in between the treatment target area and the end of the heat conductive channel as well.

In a further embodiment, the heat conductive channels extend in a direction substantially perpendicular to the light exit window. If the heat conductive channels extend into the direction substantially perpendicular to the light exit window, temperature differences between a part of the light transmitting element that is in contact with the treatment target area and a part of the light transmitting element positioned some distance away from the treatment target area are reduced.

In a further embodiment, the heat conductive channels are thermally coupled to the heat conductive layer. Thus, the heat conductive channels may receive heat from the heat conductive layer and/or may deliver heat to the heat conductive layer. The heat conductive layer provides the distribution of heat across its surface and in directions which follow at least part of the surface of the light transmitting element (e.g. substantially parallel to the treatment target area), and the heat conductive channels provide the distribution of heat in directions towards or away from the treatment target area (e.g. substantially perpendicular to the treatment target area). Thus, the combined effect of the heat conductive channels and the heat conductive layer provides an even better distribution of heat across the treatment target area. Further, if the heat conductive layer or the heat conductive channels are also thermally coupled to the light transmitting element, the whole body of the light transmitting element may receive a substantially equal temperature.

In an embodiment, distributing of heat is performed in time. For example, the heat management means may absorb heat at a first location at a first moment in time, and deliver the heat to a second location at a second moment in time. The heat may be temporarily stored by the heat management means, which allows the first location and the second location to be substantially the same location. For example, when the light source alternates between an on and off state, temporarily stored heat from the on state may be reused during the off state. When the heat distribution can be managed over time, differences between temperature distributions across the treatment target area at different operating conditions of the light therapy device may be limited, and thus temporarily cold and hot spots are prevented. Thus, the flexible light therapy device is more comfortable and safer than a flexible light therapy device without heat management means for the person who, or the animal that, is treated with the flexible light therapy device.

In an embodiment, the heat management means may comprise phase change material for temporarily storing heat. Phase change material absorbs heat when it changes from a first phase to a second phase, for example, from solid to fluid, and releases heat when it changes from the second phase to the first phase. Changing of phase generally happens at a well-defined temperature, and thus, when the temperature of the environment of the phase change material tends to increase above the well-defined temperature, heat is absorbed by the phase change material by changing from the first phase to the second phase while the temperature remains substantially the same as long as the phase change material is capable of absorbing heat. When, subsequently, the temperature of environment of the phase change material tends to decrease below the well-defined temperature, heat is released by the phase change material by changing from the second phase to the first phase and thus the temperature of the environment of the phase change material can remain substantially the same. Hence, phase change materials are effective means to buffer heat over time and thus control the heat distribution of the treatment target area. It is to be noticed that the phase change material may, in addition to storing/releasing heat, also conduct heat. The phase change material may start to change from a first phase to a second phase at a specific location and through conduction result in phase changes at neighboring locations as well, etc. When, later in time, the phase change material releases heat, the release of heat starts most probably at another specific location where the temperature tends to drop relatively fast. The locations where the absorption of the heat occurs may thus be different from the locations where the heat is released. Thus, the phase change material also distributes the heat in three dimensions.

In a further embodiment, the heat management means comprises fibers of the phase change material, the fibers provided in the light transmitting element. Thus, the fibers of the phase change material provide the distribution of heat in the light transmitting element and therefore, when the light exit window is brought in contact with the treatment target area, the heat distribution across the treatment target area is well controlled. In other embodiments, the phase change material may be arranged as small spherical elements embed in the light transmitting elements, or may be provided as a layer in between other layers of the flexible light therapy device.

The light transmitting element may comprise a light input window for receiving the light of the light source, such that more than 60% of the light is transferred towards the light exit window only via scattering and/or reflection. If most of the light is not directly transferred from the light input window towards the light exit window, the light therapy device is arranged in a so-called indirect lit configuration. Most of the light arrives at the light exit window after being reflected or scattered via the light transmitting element. Such a configuration provides a good homogeneous light distribution at the light exit window. Further, the configuration provides more design flexibility with respect to the position of the light source relatively to the light exit window, and also, a possible heat conductive coupling between the light source and the heat management means may be arranged more easily.

In an embodiment, the light transmitting element further comprises a light input window for receiving the light of the light source, wherein a plane parallel to the light input window is oriented substantially perpendicular to a plane parallel to the light exit window. The light transmitting element may be a light guide which transports light from the light input window towards the light exit window. This configuration is a so-called side-lit configuration. It is to be noted that the light guide is of a flexible material, and the plane parallel to the light input window is not necessarily a flat plane. At the position where the plane parallel to the light input window intersects the plane parallel to the light exit window, the plane parallel to the light input window is oriented substantially perpendicular to the plane parallel to the light exit window. A side-lit configuration allows the positioning of one or more light sources to be at one side of the light transmitting element, which requires less electrical wiring and allows the use of a dedicated housing for the light sources. Further, by bringing the light sources at a side it allows the light transmitting element to be as flexible as possible, which is advantageous especially when a relatively large part of the light guide has to be brought in contact with the skin of the treated person or treated animal. Further, when the light sources are all located at one side of the light guide, a common location is obtained where the heat management means may be thermally coupled to the light sources. An effectively and efficiently coupled heat management means prevents that the light guide becomes, during operation, relatively warm at one side because of the contact with the light source, or light sources, while another side of the light guide remain relatively cold.

In an embodiment, the flexible light therapy device further comprising a reflector for reflecting the light emitted by the light source towards the light input window. If the light source is directly coupled to the light input window for coupling the light in the light transmitting element, the design options for properly connecting the heat management means to the light source are limited and often a weak point. For example, if the light source is arranged in a side-lit configuration (e.g. next to the light transmitting element) and the heat management means comprises a heat conductive layer on a surface of the light transmitting element (e.g. on top of the light transmitting element), the heat conductive layer has to be bent to be thermally coupled to the light source at the side of the light transmitting element. Especially these bends are weak points. If a reflector is used to reflect the light emitted by the light source towards the light input window, the light source may be placed more conveniently for connecting to the heat management means thereby avoiding weak points (e.g. in the plane of the heat conductive layer of the heat management means).

In an embodiment, the flexible light therapy device further comprises a light management means to control a light distribution across the treatment target area.

The inventors have realized that it is advantageous to control the light distribution across the treatment target area as well. Specific therapeutic effect may be obtained by having a controlled light distribution and a controlled heat distribution. A light distribution may compensate a non-uniform heat distribution, because light is also absorbed and as such converted to heat. The light management means may also cooperate with the heat management means to obtain a specific non-uniform heat distribution which provides at specific spots of the treatment target area much more heat than at other spots.

In a further embodiment, a first sub-area of the treatment target area receives less heat than a second sub-area of the treatment target area and the light management means distributes more light to the first sub-area than to the second sub-area.

Although the heat management means may be configured to conduct heat to the treatment target area such that the heat distribution across the treatment target area becomes as uniform as possible, it is often difficult to prevent that a second sub-area of the treatment target area receives more conducted heat than a first sub-area. Especially a part of the treatment target area close to the light source is most probably warmer than other parts. By distributing more light to a sub-area, this sub-area receives more energy via radiation. Thus, more light is absorbed in this sub-area than in other sub-areas, and consequently receiving less energy via heat conduction in a certain sub-area is at least partly compensated by receiving more energy via light in that sub-area. The treated person or animal experience a more uniform heat distribution in the skin below the treatment target area, which is more convenient and results in a more uniform advantageous therapeutic effect across the whole treatment target area.

In another embodiment the light transmitting element comprises the light management means. The light transmitting element is transmitting the light from the light source to the treatment target area and as such it is an element which may be constructed such that a specific light output distribution is obtained. By using the light transmitting element for this purpose no additional elements need to be introduced in the flexible light therapy device, which saves costs and reduces the complexity of the flexible light therapy device.

In a further embodiment, the light transmitting element comprises light outcoupling structures to control the distribution of light to the treatment target area. Light transmitting elements are often elements wherein the light is captured and via total internal reflection the light is transmitted to another location. Especially when the light input window and the light exit window of the light transmitting element are not oriented opposite each other, specific measures have to be taken to stop the total internal reflection of the light and to outcouple the light via the light exit window. Means to redirect the light such that the light is outcoupled via the light exit window are called light outcoupling structures. Light outcoupling structures are often small structures which influence the reflectivity of one of the walls of the light transmitting element such that the light which impinges on the structures is reflected or scattered towards the light exit window. By configuring a specific distribution of light outcoupling structures or by constructing them in specific shapes at specific positions, the light output distribution at the treatment target area is controlled by the light outcoupling structures.

In an embodiment, the light transmitting element has a shape which is arranged to control the distribution of light to the treatment target area. The light transmitting element transmits the light from the light source towards the light exit window via reflection in that walls of the light transmitting element are often used to redirect the light towards the light exit window. By constructing the light transmitting element in a specific shape, the directions of reflection of the light is influenced so as to obtain a required light output distribution at the light exit window and, thus, at the treatment target area. In the subsequent example the light input window is positioned at a side wall of the light transmitting element and the light output window is positioned at a bottom wall of the light transmitting element. The light transmitting element is subdivided into two parts. A first part of the light transmitting element is in contact with the light input window and has a shape of a brick. A second part is contact with the first part and is not in contact with the light input window. The second part has a wedge shape. The first part mainly transmits the light via total internal reflection towards the second part. The second part reflects all the received light to the light exit window.

In a further embodiment, the reflector is arranged to provide a collimated light beam to the light input window, wherein the full width half maximum collimation angle of the collimated light beam is smaller or equal to 45 degrees. The light beam which enters the light transmitting element via the light input window has a specific distribution of angles with respect to the normal to the light input window. The collimation angle is defined as the maximum angle between one light ray of the light beam and another light ray of the light beam, wherein the one light ray and the another light ray have a specific (minimum) light intensity. If the light beam is symmetric with respect to the normal to the light input window, the collimation angle is twice the value of the maximum angle between the normal and a light ray of the light beam. The light beam which enters the light transmitting element via the light input window has a specific light intensity distribution in which the light intensity is related to the angle between the normal to the light input window and light rays of the light beam. The full width half maximum collimation angle is two times the angle at which the light intensity is half of the maximum light intensity.

If the light beam is collimated and has the full width half maximum collimation angle that is smaller than 45 degrees, most of the light rays of the collimated light beam are transmitted relatively far into the light transmitting element before one of the light rays reaches the light exit window or before another one of light rays is reflected towards the light exit window by a wall of the light transmitting element. Thus, the result is that more light is emitted through a sub-area of the light exit window which is relatively far away from the light input window. This may be advantageous in cases where the area close to the light input window becomes warmer as the result of heat directly coming from the light source. It is to be noted that the collimation angle of the light beam is measured within the light transmitting element.

According to another aspect of the invention, a plaster or a bandage is provided which comprises the flexible light therapy device according to the first aspect of the invention. The plaster or the bandage provides the same benefits as the flexible light therapy device according to the first aspect of the invention and has similar embodiments with similar effects as the corresponding embodiments of the device.

These and other aspects of the invention are apparent from and will be elucidated with reference to the embodiments described hereinafter.

It will be appreciated by those skilled in the art that two or more of the above-mentioned embodiments, implementations, and/or aspects of the invention may be combined in any way deemed useful.

Modifications and variations of the device, which correspond to the described modifications and variations of the system, can be carried out by a person skilled in the art on the basis of the present description.

Figure 1:
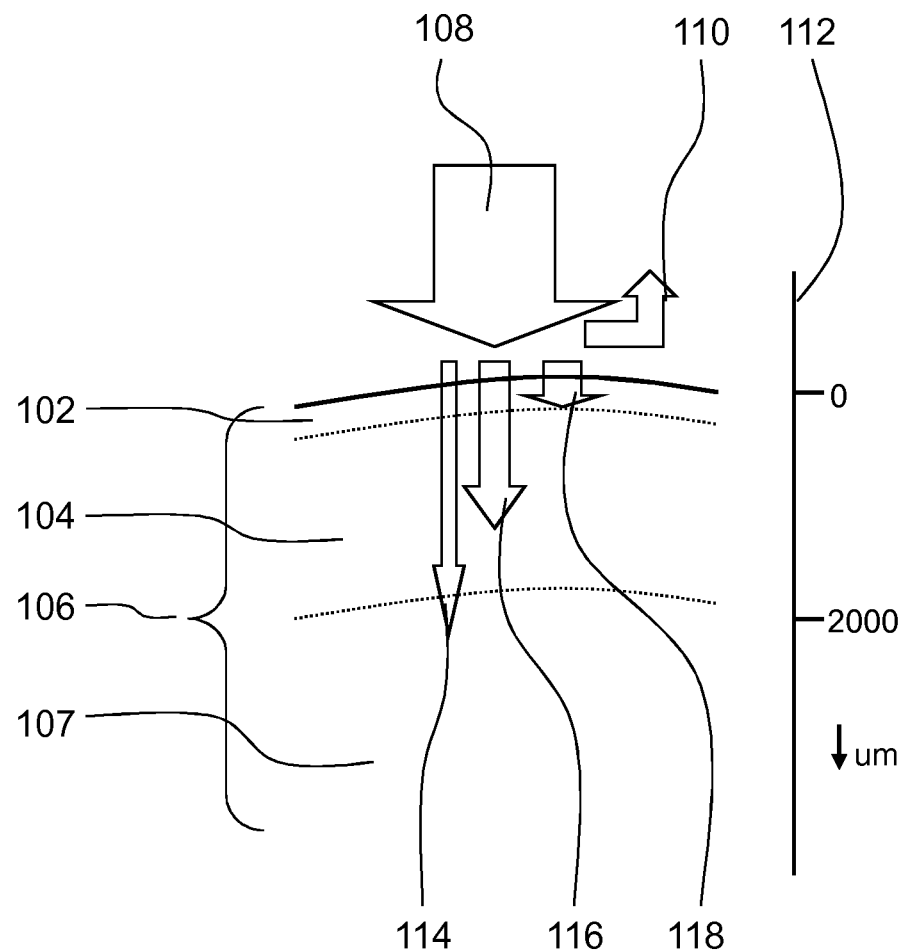
FIG. 1 schematically shows a cross-section of the human skin.

It should be noted that items denoted by the same reference numerals in different Figures have the same structural features and the same functions. Where the function and/or structure of such an item have been explained, there is no necessity for repeated explanation thereof in the detailed description.

The figures are purely diagrammatic and not drawn to scale. Particularly for clarity, some dimensions are exaggerated strongly.

DETAILED DESCRIPTION OF THE EMBODIMENTS

In FIG. 1 a cross-section of the human skin 106 is shown. The top layer of the human skin 106 is the epidermis layer 102. Below the epidermis layer 102 is the dermis layer 104, below which the subcutis layer 107 is present. The dermis layer 104 has a lot of heat sensors. If the heat sensors experience heat, the human body may react with a vasodilatory response which locally enhances the blood circulation in the skin and in areas near to the experienced heat.

At the right end of the figure an axis 112 is provided which shows the thickness of the layers in micrometers (μm). It is to be noted that the thickness of the layers may vary depending on the specific location of the skin 106 on the body.

When light 108 of a specific spectrum of wavelengths impinges on the skin 106, a part 110 of the light is reflected. Specific wavelengths penetrate deeper in the human skin 106 than other wavelengths, because these other wavelengths are absorbed by specific layers of the skin 106. In an example, a relatively large part 118 of the light is absorbed by the epidermis layer 102. Another part of the light 116 penetrates to the dermis layer 116 before being absorbed. A relatively small part 114 may penetrate into the subcutis layer 107 before being absorbed. The absorption of the light results in a heating effect of the respective epidermis layer 102, dermis layer 104 and the subcutis layer 107. Infrared A light (800-1500 nm) may penetrate relatively deep into the skin, up to the subcutis layer 107, and therefore the heat sensors do not sense much of the heat generated by the absorption of this Infrared A light. Other wavelengths in the infrared spectrum may be absorbed in the top layers.

Today, light therapy devices often comprise light sources which emit most of the light in a spectrum visible to the human eye. They may in addition comprise light sources which emit for example light in the Infrared spectrum. Light Emitting Diodes (LEDs) or Organic Light Emitting Diodes (OLEDs) have the beneficial effect of generating the light relatively efficiently with relatively cheap devices. LEDs and OLEDs are relatively small compared to for example Infrared lamps and thus they are well suited for integration in a flexible light therapy device. The light 108 may, in operation, be used to warm up the skin 106 of the treatment target area. The spectrum is such that at least a part of the light is transmitted into the deeper layers of the skin 106 to warm up the deeper layers to obtain a well-being and/or therapeutic effect. In the visible spectrum blue light (400-470 nm) is less reflected by the skin than other colors in the visible spectrum. Further, blue light is mostly absorbed in the dermis layer 104 and the epidermis layer 102 of the human skin 106 and thus the warmth resulting from the absorption of blue light is perceived well by the heat sensors. The heat sensation results in a well-being feeling and in a health effect because of the enhanced blood circulation.

Figure 2A:
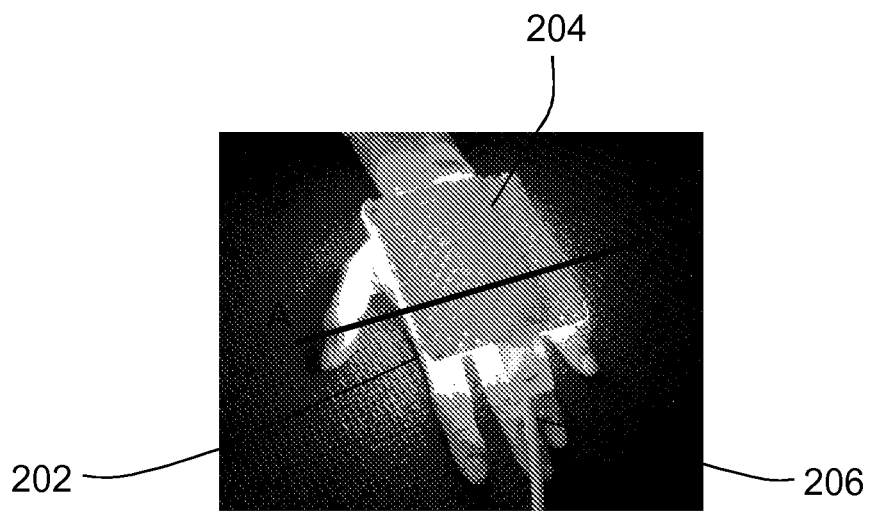
FIG. 2a shows a photograph of a light patch which is a first embodiment of the flexible light therapy device according to the first aspect of the invention, FIG. 2b schematically shows a cross-section of the light patch of FIG. 2a, FIG. 3a schematically shows a cross-section of a second embodiment of a flexible light therapy device, FIG. 3b schematically shows another cross-section of the second embodiment, FIG. 4 schematically shows a cross-section of a third embodiment, FIG. 5a-5d schematically show a cross-section of a fourth to seventh embodiment of the flexible light therapy device, respectively, FIG. 6a schematically shows a cross-section of an eighth embodiment of a flexible light therapy device, FIG. 6b schematically shows another cross-section of the eighth embodiment of the flexible light therapy device, FIG. 7a schematically shows an embodiment of a plaster according to the second aspect of the invention, FIG. 7b schematically shows an embodiment of a bandage according to the third aspect of the invention, FIG. 8 schematically shows another cross-section of an embodiment of a flexible light therapy device, FIG. 9a-9d schematically show cross-sections of embodiments of a flexible light therapy device that comprise a light management means, and FIG. 10 schematically shows a cross-section of another embodiment of a flexible light therapy device that comprises a light management means.

A first embodiment of the invention is shown in FIG. 2a. FIG. 2a shows a photograph of a flexible light patch 204. The flexible light patch 204 is brought in contact with the back of a hand 202. The flexible light path 204 comprises LEDs which emit blue light into a light guide. The light guide transfers a substantially large amount of the light into the direction of the back of the hand 202 and the light impinges on the skin of the hand 202. The flexible light patch 204 is connected via a power cable 206 to a source of electrical energy. In another embodiment, the flexible light patch 204 comprises a battery for providing electrical energy to the LEDs. At the top surface of the flexible light patch 204, which is the surface opposite the surface where the flexible light patch 204 is in contact with the hand 202, there is provided with a flexible heat conductive material which is thermally coupled to the LEDs and which is thermally coupled to the light guide.

Figure 2B:
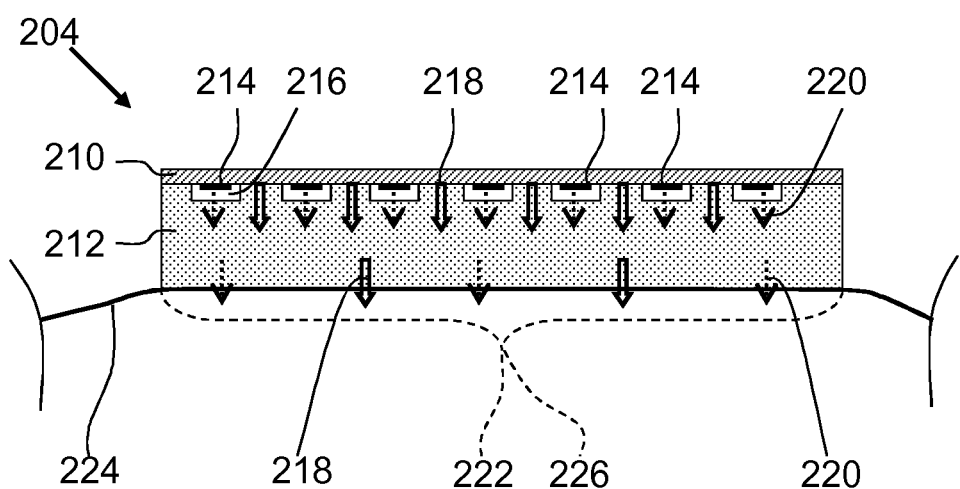

FIG. 2b shows a cross-section of the flexible light patch 204 along line A-A' which is drawn in FIG. 2a. The flexible light patch 204 comprises a light guide as the light transmitting element 212 which is made of a flexible light transmitting material. "Light transmitting" means that at least a part of the light that enters the light guide also leaves the light guide. The light guide is flexible to allow bending the flexible light patch 204 along the curves of the body of a human being or an animal. A plurality of LEDs 214 is provided in small cavities 216 of the light transmitting element 212. The LEDs 214 emit light 220 into the light guide. The light 220 has a specific spectrum. Almost all the light 220 which is emitted by the LED 214 into the light guide is coupled out through a light exit window 222 towards the skin 224 of a person or an animal. In the example shown, the flexible light patch 204 is brought in contact with the skin 224. Because the flexible light therapy device may be used for persons and animals, in the following description the terms person, human being and animal may be interchanged. The part of the skin 224 facing the light exit window 222 is referred to as the treatment target area 226. In operation, layers of the skin 224 at the treatment target area 226 warm up and as such a well-being and therapeutic effect is provided to the treated person. In the shown configuration, which is called the direct-lit configuration, the light 220 is transmitted almost directly through the light transmitting element 212 towards the light exit window 222. At a surface of the light transmitting element 212 opposite the light exit window 222 a flexible heat spreading layer 210 is provided. The flexible heat spreading layer 210 is thermally coupled to the light guide and is thermally coupled to the LEDs 214. The flexible heat spreading layer is arranged to distribute heat across the top surface of the light transmitting element (i.e. opposite the light exit window 222), thereby also controlling the heat distribution in the body of the light transmitting element and across bottom surface of the light transmitting element (i.e. the light exit window 222 itself). Without the heat spreading layer 210, the flexible light path 204 would be warmest near the LEDs 214. The heat spreading layer 210 receives the residual heat of the LEDs 214 and transports the heat 218 across the whole of the light transmitting element 212. The light transmitting element 212, which has a specific thermal capacity and a specific thermal conductivity, receives the heat 218 from the flexible heat spreading layer 210, stores some of the heat temporarily and conducts the rest towards the light exit window 222. Thus, the heat distribution across the light exit window 222 becomes more uniform and a higher average temperature is obtained at the light exit window 222 due to reuse of the residual heat from the LEDs. At the light exit window 222 an amount of heat is conducted towards the skin of the treated person when the flexible light patch 204 is brought in contact with the skin.

The flexible light patch 204 does not only provide a therapeutic effect by radiating electromagnetic waves into the layers of the skin 224 such that the heat sensors in the layers of the skin perceive a heat sensation, the flexible light path 204 also provides heat via conduction to the skin 224 which results in an improved heat sensation. Further, because of the better controlled heat distribution at the light exit window 222, the flexible light patch 204 is safer for the treated person, i.e. the probability that hot spots which have a temperature above a safe skin contact temperature are present at the light exit window 222 is much lower. Further, the residual heat of the LEDs 214 is not wasted and is used efficiently to increase the therapeutic effect. By carefully dimensioning the amount of energy transferred via radiation and the amount of energy transferred via heat conduction, electrical energy may be saved. It is, for example, possible to alternate between the on and off state of the LEDs 214, while the treated person still perceives an advantageous warmth sensation which is provided by the heat that was temporarily stored in the specific heat capacitance of the light transmitting element.

The flexible light patch 204 comprises a plurality of LEDs 214 which emit light of a specific spectrum that has advantageous well-being and/or therapeutic effects. The spectrum is not limited to visible light or light of a single primary color. The spectrum may, for example, comprise electromagnetic waves in the infrared spectrum as well. Embodiments of the flexible light patches 204 are not limited to comprising a plurality of LEDs 214. Other light sources may be used as well, like Organic Light Emitting Diodes (OLEDs), solid state lasers, gas discharge tubes, or incandescent lamps. In a specific embodiment only one light source is used which is a flexible OLED which partially covers the light exit window 222.

Figure 8:
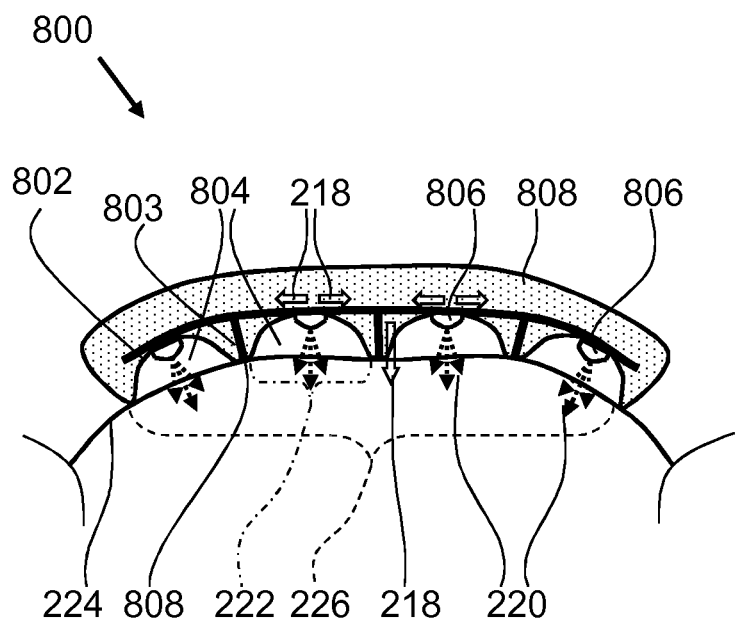

The light exit window 222 advantageously is at least 90% of the area of the light transmitting element 212 that is brought in contact with the skin 224 of the treated person. The light exit window 212 may have a size of a few square centimeters up to a size of a body of a human being. If the light exit window is as large as a body of a human being, the flexible light therapy device may be incorporated in a blanket or in a mat such that a person may lay under the blanket or on the mat while being treated. The flexible light therapy device may also be integrated in clothes, like for example pajamas. Further, the light transmitting element 212 is manufactured of a flexible light transmitting material, for example silicone, a light transmitting nonwoven or woven fabric, or an aerogel. The flexibility of the flexible light transmitting material is high enough to allow the bending of the flexible light therapy device such that an effective optical and thermal coupling to the treatment target area 226 is obtained. The light transmitting element may also be manufactured as illustrated in FIG. 8, discussed later on, wherein a flexible foam material 808 comprises cavities 804 for transmitting the light 220 from the light sources 806 to the light exit window 222. "Light transmitting" means that light which is received from the light source 214 is at least partially transmitted towards the light exit window 222. The light transmitting material may be transparent or translucent. The light transmitting material may further filter, diffuse or scatter the light. Like every material, the light transmitting material has a specific heat capacity and a specific heat conductivity. Thus, some heat may be stored in the light transmitting element 212 and some heat may be conducted through the light transmitting element 212 and so the light transmitting element 212 not only influences light distribution at the treatment target area 226 but may also influences the heat distribution across the treatment target area 226. In the shown embodiment of FIG. 2b, the heat management means 210 controls the heat distribution at the treatment target area 226 indirectly by using the light transmitting element 212 as a medium capable of transferring heat towards the treatment target area 226. Similarly, the foam material 808 and air cavities 804 of the light transmitting element of FIG. 8 may be adapted to transfer heat from the heat management means 802, 803 towards the treatment target area 226. In another embodiment, controlling the heat distribution at the treatment target area may be performed directly when for example the heat management means 210 is brought in direct contact with the treatment target area 226, or combinations of direct and indirect control of the heat distribution is possible. It is to be noted that the heat management means 210 and the light transmitting element 212 are different components of the flexible light therapy device. However, they may be assembled such that they seem to be one unit, for example, by interweaving the materials of both components.

Figure 3A:
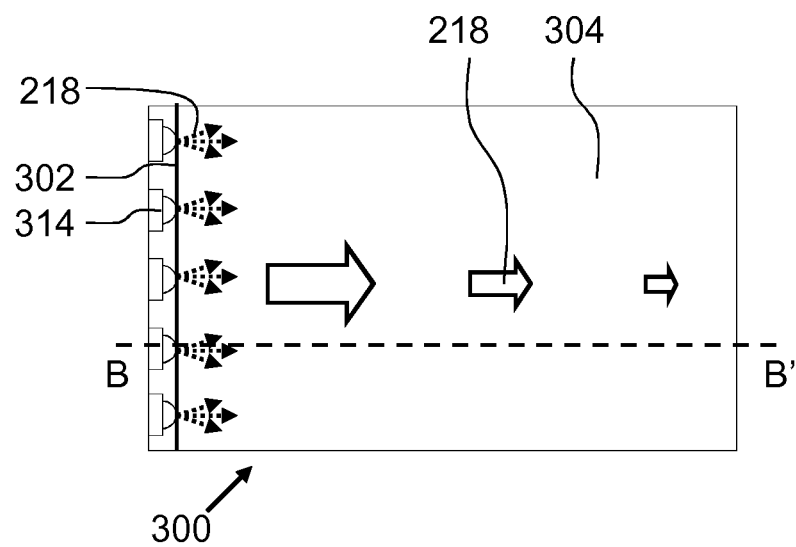
Figure 3B:
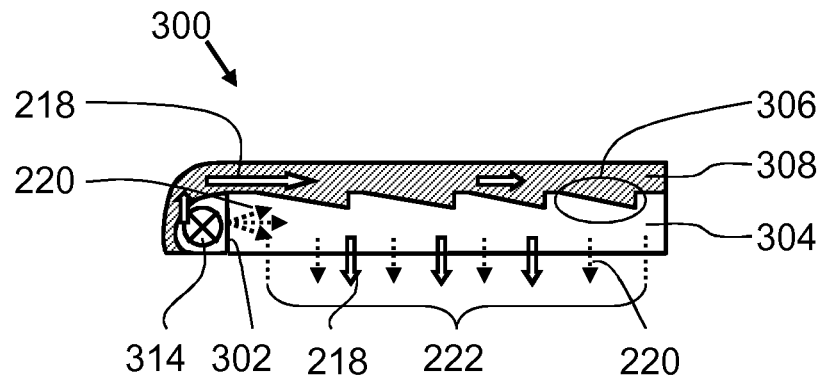

FIGS. 3a and 3b show another embodiment of a flexible light therapy device 300. The shown embodiment shows a side-lit configuration. FIG. 3a shows a schematic cross-section of the light therapy device 300 in the x-y plane, assuming that the x-y plane is parallel to the light exit window 222. FIG. 3b shows a schematic cross-section of the light therapy device 300 across line B-B' that is drawn in FIG. 3a. The light sources 314 emit light 220 via a light input window 302 into a light transmitting element 304, which in side-lit configurations is frequently referred to as a light guide. The light sources 314 may be LEDs or other types of light emitters. It is even possible to have one light emitter, for example a gas-discharge lamp in the form of an elongated tube. The light guide 304 is manufactured of a flexible light transmitting material, for example silicone. The light guide 304 has light redirection structures 306 which reflect the light 220 that is received at the light input window 302 towards the light output window 222 where it is coupled out from the light guide 304. A plane which follows the light input window 302 has a substantially perpendicular orientation with respect to a plane which follows the light output window 222. The light transmitting element 304 is partly covered with a heat management means 308 for distributing heat. The heat management means 308 may be a flexible heat conducting material and is thermally coupled to the light guide 304 and to the light sources 314 and distributes heat 218 from locations with a higher temperature, e.g. near the light sources, to locations with a lower temperature, e.g. more remote from the light sources. The high temperature locations may for example be the heat sink of the light sources or warm spots in the light guide. The light guide 304 is also capable of conducting heat 218, depending on its specific heat conductivity, and as such heat 218 can flow from the light sources 314 via the flexible heat conductive material 308 and the light guide 304, towards the light exit window 222. In use the light exit window 222 is brought in contact with the treatment target area and as such the heat distribution across the treatment target area can be better controlled. The heat management means 308 may be of such a material that the interface between the light guide 304 and the heat management means 308 is light reflective such that the redirecting of light by the redirecting structures 306 is more effective. The flexible heat conductive material 308 may for example be a flexible metallic material which is deposited on the light guide 304, or the flexible heat conductive material 308 may be silicone that contains a high concentration of metal particles.

Figure 4:
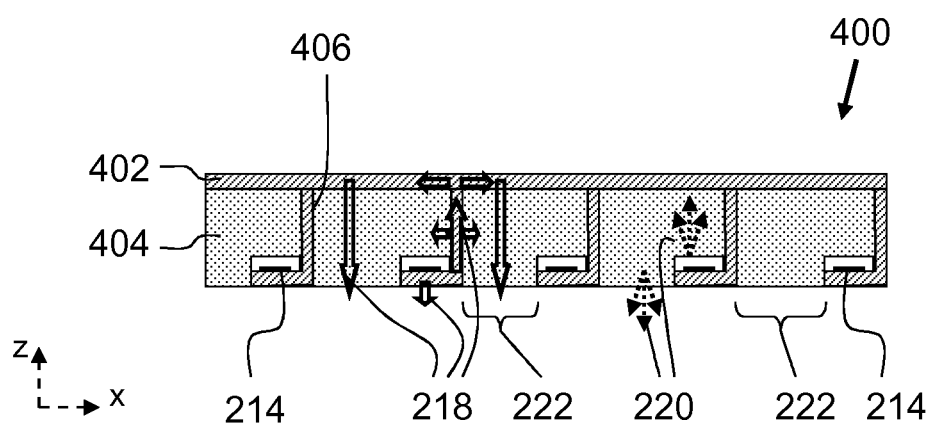

FIG. 4 shows a schematic cross-section of another embodiment of a flexible light therapy device 400. The flexible light therapy device 400 comprises a light transmitting element 404. In the light transmitting element 404 are provided LEDs 214 which emit light 220 of a specific spectrum into the light transmitting element 404 (see upward oriented arrows in FIG. 4). The light 220 is reflected back at a top surface of the light transmitting element 404 and is, consequently, transmitted towards one of the light exit windows 222 (see downward oriented arrows in FIG. 4). This configuration of light sources in a light emitting device is also known as an indirect-lit configuration. The light exit windows 222 are in contact with the treatment target area of the skin of a treated person when the light therapy device is in use. The LEDs 214 are in contact with a heat conductive material formed as heat conductive channels 406 through the light transmitting element 404. The heat conductive channels 406 are in contact with a heat spreader 402 which is provided at a side of the flexible light therapy device 400 that is opposite to the light exit windows 222. A part of the heat generated by the LEDs 214 is directly transmitted to the skin of the treated person, and another part is conducted via the heat conductive channels 406 towards the heat spreader 402. In this embodiment the heat conductive channels 406 and heat spreader 402 may be regarded as the heat management means. The heat spreader 402 distributes the heat in a plurality of directions across the top surface of the light transmitting element 404 such that, via the thermal contact between the heat spreader 402 and heat conductive channels 406 on the one hand and the light transmitting element 404 on the other hand, the whole light transmitting element 404 warms up and hence an additional uniform distribution of heat is conducted towards the light exit windows 222 and thus towards the treatment target area. It is shown in FIG. 4 that the heat conductive channels 406 and the heat spreader 402 distribute the heat such that temperature differences within the light transmitting element 404 are reduced such that the heat distribution at the light exit window is made more uniform. It is to be noted that the size of the light exit windows 222 is preferably relatively large compared to the size of the LED mounting areas such that (i) the light distribution exiting the light therapy device at the treatment target area is 'felt' as substantially uniform and (ii) the impact of possibly local hot spots underneath the LEDs mounting area is minimal.

The heat spreader 402 may be of a light reflecting heat conductive material to effectively distribute the heat and to reflect the light 220 of the LEDs 214 effectively towards the light exit windows 222. The heat conductive channels 406 may be channels in the form of holes, tubes or beams, or they may be formed by cuts such that light chambers are created within the light guide. Heat conductive channels 406 may comprise metal wires, graphite sheets or a heat conducting paste. Further, it is advantageous to have heat conductive channels comprising a heat conduction as well as light reflecting material to prevent absorption of light in the heat conductive channels. In another embodiment, the walls of the heat conductive channels are provided with a reflective coating.

It is to be noted that, in another embodiment of the flexible light therapy device 400 of FIG. 4, the flexible light therapy device 400 may not comprise heat conductive channels 406. In that case, only the heat spreader 402 assists in the distribution of the heat such that a more uniform heat distribution is obtained in the light transmitting element 404. However, it is expected that the surface of the light transmitting element which is in contact with the skin of the person and is located close to the LEDs 214 is still significantly warmer than the surface of the light guide which is not located close to the LEDs 214. It was found in heat budget calculation that the heat conductive channels 406 are also an effective means to manage the heat distribution through the whole flexible light therapy device 400.

It is further to be noted that in other embodiments the heat spreader 402 and/or the heat conductive channels 406 are not necessarily thermally coupled to the light transmitting element 404 but used to distribute the heat uniformly across the light therapy device 400. The heat conductive channels 406 distribute the heat in the indicated z-direction, and the heat spreader 402 distributes the heat in the indicated x-direction and the y-direction (which is the direction perpendicular to the plane of the drawn figure), irrespective of the location of the heat source, uniformly across the light therapy device 400.

The heat conductive channels 406 may be arranged to be thermally coupled to the treatment target area such that heat is in this way also distributed across the treatment target area.

It is to be noted that the heat conductive channels 406, as drawn in FIG. 4, may also be present in the embodiment of the flexible light therapy device 204 of FIG. 2a and FIG. 2b. The flexible light therapy device 204 may have heat conductive channels which are thermally coupled to the heat spreader 210 and which extend between the heat spreader 210 and the light exit window 222.

Figure 5A:
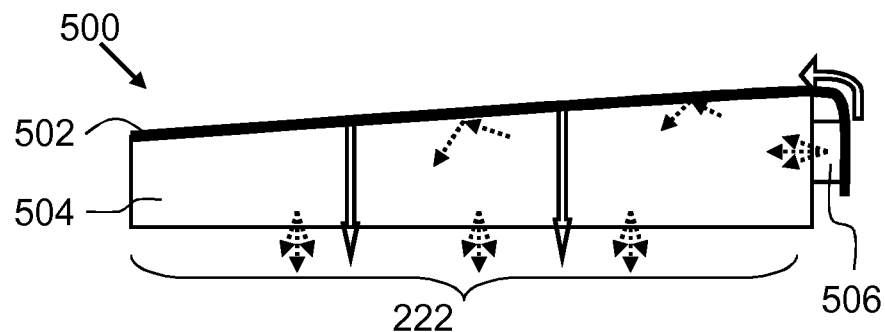
Figure 5B:
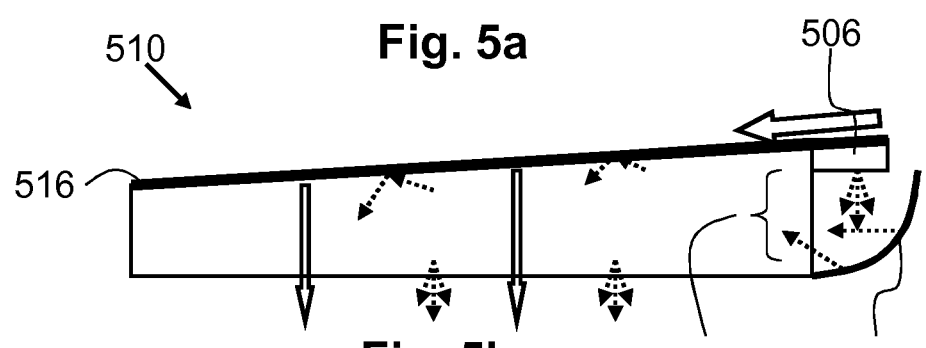
Figure 5C:
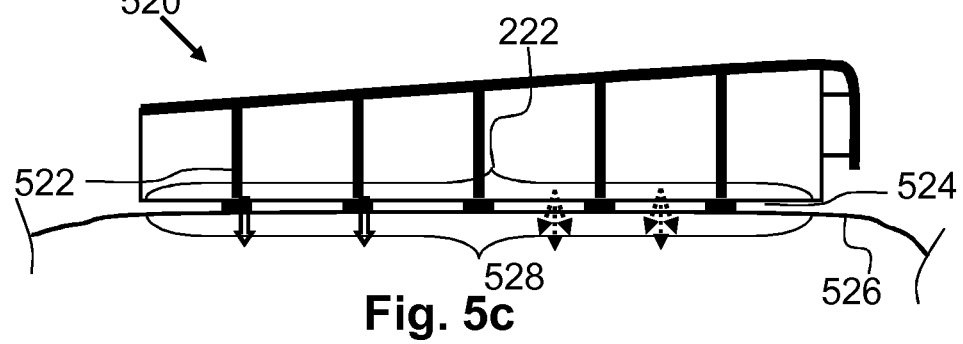
Figure 5D:
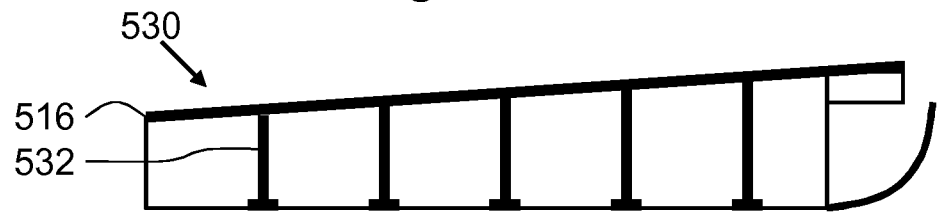

FIGS. 5a to 5d schematically show cross-sections of other embodiments of the invention. In FIG. 5a there is provided a flexible light therapy device 500 comprising a light guide 504 and a flexible heat spreader 502, for distributing heat, which is thermally coupled to the light guide 504. The light guide 504 has a light exit window 222 and the light guide 504 receives light from a light source 506. The light source 506 is also thermally coupled to the heat spreader 502. The light guide is slightly tapered such that the surface between the light guide 504 and the heat spreader 502 reflects the received light towards the light exit window 222. The residual heat of the light source 506 is distributed by the heat spreader 502 across the light guide 504 and as such the heat distribution across the light exit window is better controlled. The heat spreader 502 prevents that a part of the light exit window close to the light source 506 becomes substantially warmer than a part of the light exit window 222 positioned at another end of the light guide. In the flexible light therapy device 510 of FIG. 5b the light source 506 is emitting the light into the direction of a reflector 512 which reflects the light towards a light input window 514 of the light guide. The use of a reflector 512 prevents that the heat spreader 516 needs to be bend close to the light source 506, creating a sharp curve in the heat spreader which is always sensitive to cracks or damage. The flexible light therapy device 520 of FIG. 5c is roughly the same as the flexible light therapy device 500 of FIG. 5a. However, the flexible light therapy device 520 is provided with heat conductive channels 522 which extend in a direction which is substantially perpendicular to the light exit window 222. The heat conductive channels 522 are arranged for being brought in contact with the treatment target area 528 of the skin 526 of a person. The heat conductive channels 522 protrude from the light guide 504 and thus a small air gap 524 is present between the skin 526 of the person and the light guide 504. Thus, light from the light source 506 is emitted through the light exit window 222 of the light guide towards the treatment target area 528 via radiation and heat from the light source 506 is primarily conducted via the heat spreader and heat conductive channels 522 towards the treatment target area 528, but heat may also be conducted through heat radiation from the light guide body, which is in thermal contact with the heat spreader and heat conductive channels 522, towards the treatment target area 528. It is to be noted that in an alternative embodiment of the flexible light therapy device 520 the air gap 524 is not present between the light guide 504 and the skin 526 of the person. In yet another embodiment of the flexible light therapy device 520, the heat conductive channels 522 do not protrude from the light guide 504 and do not end at the light exit window 222, but end close to the light exit window 222. In this embodiment the heat conductive channels 522 are thermally coupled to the light guide 504 and significantly improve the heat distributed across the light guide 504 and, via the light guide, towards the treatment target area 528. The flexible light therapy device 530 of FIG. 5d is roughly the same as the embodiment of FIG. 5b, however, it is provided with additional heat conductive channels 532 which provide a better heat conduction from the heat spreader 516 to the treatment target area. Similar comments as for FIG. 5c can be made for FIG. 5d.

Starting from an intended therapeutic effect, which is a combination of light and heat, to be provided to the treatment target area and taking into account the ability of elements of the flexible light therapy device to conduct, distribute and/or store heat, the light source(s) can be selected such that a maximum amount of heat from the light source(s) is (re)used for therapeutic purposes and heat sinking away from the light therapy device and the light exit window is minimized. Hence, no cooling mechanism which transfers heat to the ambient is required and the flexible light therapy device may be safely used under clothing.

Figure 6A:
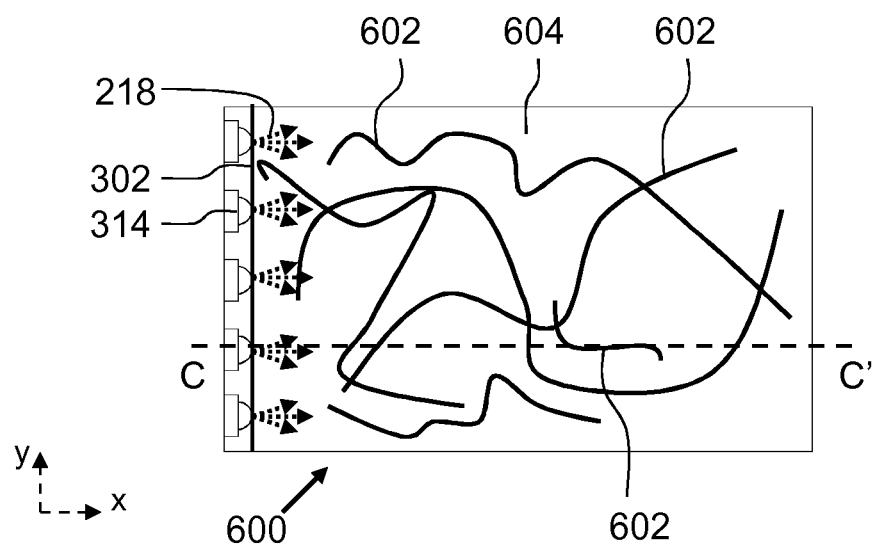
Figure 6B:
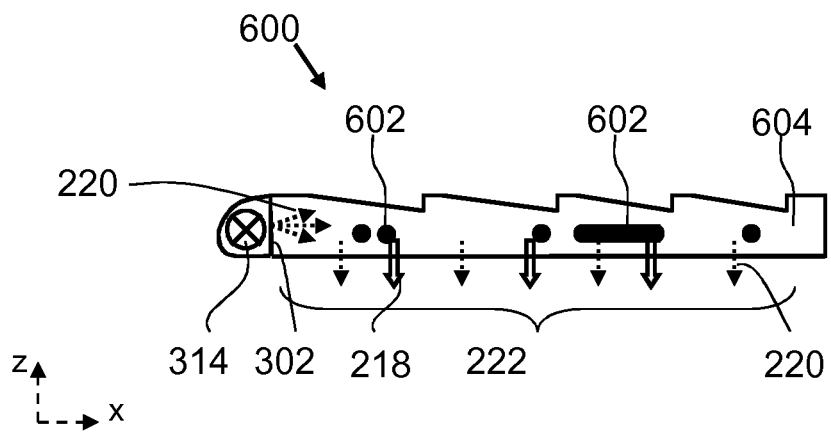

FIG. 6a shows a schematic cross-section along an x-y plane of a flexible light therapy device 600 and FIG. 6b shows a cross-section along line C-C' that is drawn in FIG.

6a. The light therapy device 600 has, from its appearance, a similar setup as the light therapy device 300 of FIG. 3a and FIG. 3b. However, the light therapy device 600 has a heat management means which comprises fibers or channels 602 of a phase change material provided in the light guide 604. The phase change material absorbs heat when it changes from a first phase to a second phase at a phase change temperature, and releases heat when it changes from the second phase to the first phase at substantially the same phase change temperature. If there is a heat flux towards the fibers or channels 602 such that the temperature around the fibers or channels 602 tends to rise above the phase change temperature, the phase change material absorbs the heat thereby slowing down or reducing the temperature rise. When there is a heat flux away from the fibers and channels 602 such that the temperature around the fibers or channels 602 tends to sink below the phase change temperature, the phase change material releases heat thereby reducing the temperature drop. Thus, the phase change material temporarily stores heat and is, consequently, used to obtain a more stable temperature in the light guide 604 over time. Further, the phase change material is often a better heat conductor than the material of the light guide itself and, thus, the fibers or channels 602 also transfer heat between different locations in the light guide realizing an improved 3-dimensional heat distribution across the light guide, which is an additional advantageous effect. In an example, the phase change material is paraffin or comprises fatty acids. In other embodiments small spheres of the phase change material are integrated or dispersed in the light guide 604, or a layer of a phase change material is provided within the light guide 604. Also the heat conductive channels described with other embodiments such as those with reference to FIGS. 4 to 5d may also comprise a phase change material. It is to be noted that in the embodiment shown in FIGS. 6a and 6b the light guide 604 provides the thermal coupling between the light source 314 and the fibers or channels 602 with the phase change material. In an alternative embodiment at least a part of the fibers or channels 602 end at the light input window 302 such that the fibers or channels 602 are directly thermally coupled to the light source 314.

It is to be noted that the fibers or channels 602 filled with the phase change material or the spheres of phase change material may also influence the optical parameters of the light transmitting element. For example, if paraffin is used, and if the paraffin is in the solid state, the paraffin assists in scattering the light within the light guide 604. If the paraffin is in the fluid state some light may be transmitted via the paraffin to another location in the light guide 604.

Figure 9A:
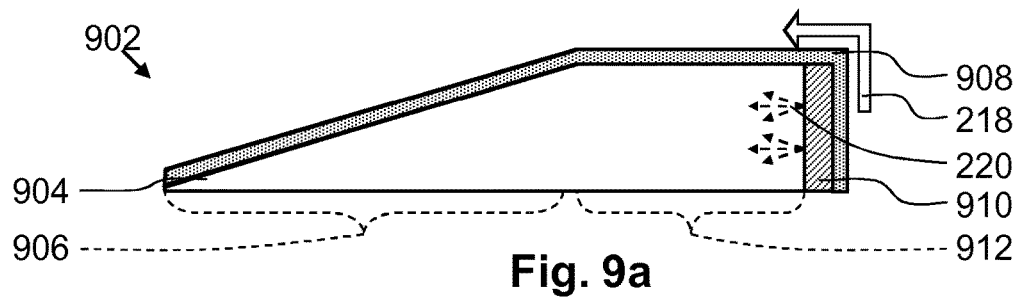

FIG. 9a shows a cross-cut of en embodiment of a flexible light therapy device 902 which comprises a light transmitting element in the form of a light guide 904. The light guide 904 comprises a light transmitting flexible material receives light 220 from a light source 910. The flexible light therapy device 902 is configured in a so-called side-lit configuration, wherein the light input window of the light guide 904 has an orientation that is substantially perpendicular to the light exit window of the light guide 904. The flexible light therapy device 902 further comprises a heat management means in the form of a heat conductive layer 908. The heat conductive layer 908 is thermally coupled to the light source 910 and is applied to a surface of the light guide 904 which is opposite the light exit window of the light guide 904. The shape of the light transmitting element 904 is such that a specific light output distribution is obtained at the light exit window. In the cross-section it is seen that the light transmitting element 904 consists of a first part which is located adjacent to the light source wherein the thickness of the light transmitting element remains constant. A second part of the light transmitting element 904 that is further away from the light source, has a wedge shape, which means that the thickness reduces at distances further away from the light source.

With respect to the thermal management in this embodiment, a first sub-area 912 of the light exit window receives a relatively large amount of heat from the light source via the indirect path from the back of the light source 910 via the heat conductive layer 908 and through the light guide 904 and via a direct path from the front of the light source 910 through the light guide 904. At a second sub-area 906 of the light exit window heat is substantially only received via a path through the heat conductive layer 908 and the light guide 904 and as such the second sub-area 906 receives less heat than the first sub-area 912. Receiving less or more heat is used in the meaning of receiving less or more heat per unit-area of the exit window.

The surface of the light guide 904 which contacts the heat conductive layer 908 acts as a mirror for the light which is transmitted through the inner body of the light guide 904 and which impinges on this surface. The light is substantially reflected towards the light exit window. In the first part of the light guide 904, light which entered the light guide at the light input window, which is located at the interface between the light source 910 and the light guide 904, is mainly transmitted through this part of the light guide 904 and only a limited amount of light is reflected towards the light exit window. In the second part of the light guide 904, which is the part with the wedge shape, the light received from the first part of the light guide 904 hits the upper surface the light guide 904 and is thus reflected towards the light exit window. Thus, in the first sub-area 912 a limited amount of light is distributed to the treatment target area, and in the second sub-area 906 a relative large amount of light is distributed to the treatment target area. Light which impinges on the skin of a person is absorbed in one of the layers of the skin.

Taking both the light distribution and thermal distribution at the light exit window into account, the skin which is in contact with the first sub-area 912 of the light exit window becomes relatively warm as the result of direct heat transfer from the light source 910 and is only warmed up a little bit more as the result of the absorption of light, whereas the skin which is in contact with the second sub-area 906 becomes relatively warm as the result of the absorption of light, and only a relatively small amount of additional heat is received via conduction. The heat management means 908 and light transmission element 904 therefore complement each other in providing a uniform heat distribution in the skin at the treatment target area.

Figure 9B:
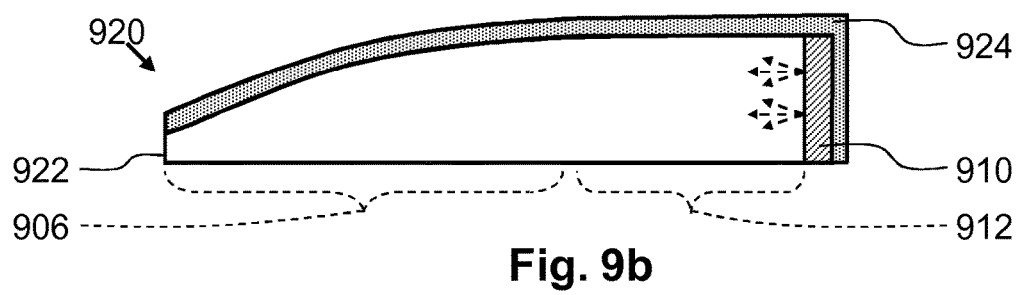

In FIG. 9b an embodiment of a flexible light therapy device 920 is shown which is a variation on the flexible light therapy device 902 of FIG. 9a. The light transmitting element 922 of the embodiment is provided such that more light is coupled out at the second sub-area 906 of the light exit window and less light is coupled out in the first sub-area 912. The thickness of the light transmitting element 920 decreases together with an increasing distance from the light source 910. The relation which describes the thickness of the light transmitting element 922 as a function of the distance to the light source 910 is a continuous function which has a continuous first derivative. In the embodiment of FIG. 9a the first derivative of such a function is not continuous. In other words, the thickness of the light transmitting element 922 gradually decreases, while the thickness of the light transmitting element 904 of FIG. 9a is initially constant and at a certain distance from the light source 910 the thickness linearly decreases towards zero. A heat conductive layer 924 is provided on top of the light transmitting element 922 and the interface between the light transmitting element 922 and the heat conductive layer 924 acts as a reflecting surface. It is to be noted that this reflection may be reflection according to the law of "angle of incidence is equal to the angle of reflection", and that this reflection may also be based on scattering the light. At larger distance from the light source 910 more light impinges on the interface between the between the light transmitting element 922 and the heat conductive layer 924 and thus more light is reflected towards the light exit window.

Figure 9C:
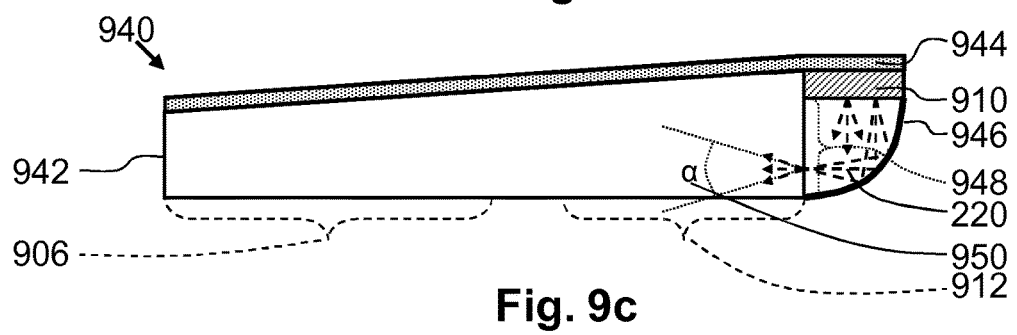

In FIG. 9c a cross-section of another embodiment of a flexible light therapy device 940 is shown. As in the embodiments of FIG. 9a and FIG. 9b, the flexible light therapy device 940 has less light output at the first sub-area 912 of the light output window than at the second sub-area 906 of the light output window. The flexible light therapy device 940 has a light source 910 which emits light towards a reflector 946. The shape of the reflector is arranged such that the light beam which is incident on a light input window 948 of a light guide 942, is to a large extent collimated, which means that a relatively large portion of the light rays of the light beams have a relatively small angle with the normal to the light input window 948, and thus a relatively small portion of the light enters the light guide 942 at a relatively large angle with respect to the normal to the light input window 948. It is to be noted that in this case a maximum amount of the light energy in the collimated light beam is transmitted in light rays which are perpendicular to the light input window. If the light enters the light guide 942 in a substantially collimated beam more light will be transmitted relatively far into the light guide without impinging on any of the outer surface of the light guide 942 and if impinged more light in the light guide 942 will be subject to total internal reflection. Only when light impinges on the surface between the light guide 942 and a heat conductive layer 944, the light is scattered or reflected towards the light exit window.

In FIG. 9c an angle α is indicated. The two light rays between which the angle α is indicated are the light rays which have an angle α/2 with the normal to the light input window at which the emitted light intensity of the light intensity distribution of the collimated light beam is half the maximum emitted light intensity of the light intensity distribution of the collimated light beam. The whole angle α is the collimation angle of the collimated light beam. In an advantageous embodiment the angle α is smaller than 45 degrees. In further advantageous embodiment the angle α is smaller than 30 degrees such that the light is transmitted over a longer distance through the light guide 942 before the light is being coupled out through the light exit window. It is to be noted that the collimation angle α of the collimated light beam is measured in the light guide material. If the light guide is, for example, made of silicon, the refraction index of the silicon material is about 1.4, and if the material between the reflector 946 and the light input window 948 is air with a refraction index of 1, the collimation angle of the light beam within the air has to be less than 78 degrees in order to have the collimation angle α within the light guide 942 less than 45 degrees, after refraction of the light rays at the interface between the air and the light guide 942. In another embodiment, the area between the light source 910, the reflector 946 and the light input window 948 is filled with silicon as well. If this is the case the light rays are not refracted at the light input window 948 and thus the collimation angle of the light beam after reflection by the reflector 946 is the same as the collimation angle α within the light guide 942.

Figure 9D:
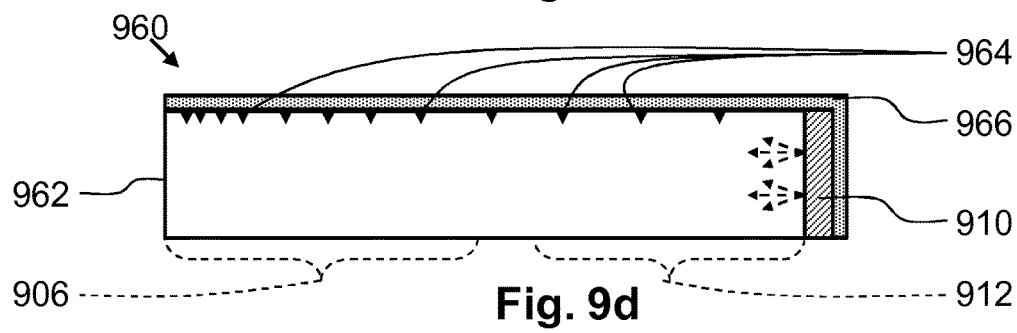

In FIG. 9d a cross-section of another embodiment of a flexible light therapy device 960 is shown. A light transmitting element in the form of a light guide 962 and a light source 910 are arranged in a so-called side-lit configuration. The light guide 962 has a rectangular cross-cut section, but may also have a shape which is similar to that of the embodiment of FIG. 9c. Heat of the light source 910 is conducted by a heat conductive layer 966 towards all parts of the light guide 962. The heat conductive layer 966 is applied to a surface of the light guide 962 that is opposite the light exit window and the heat conductive layer 966 is thermally coupled to the light guide 962 at this surface. The interface between the light guide 962 and the heat conductive layer 966 acts as a reflector and light which impinges on this layer is reflected according to the law of "angle of incidence is equal to the angle of reflection". This allows the light which is captured in the light guide 962 to be transmitted via total internal reflection to positions further away from the light source 910. The light guide 962 is further provided with light outcoupling structures 964. The light which impinges on the light outcoupling structures is either reflected or scattered towards the light exit window. As seen in FIG. 9d the distribution of the light outcoupling structures 964 is such that the further away from the light source 910, e.g. towards the sub-area 906 of the light exit window, the denser the light outcoupling structure distribution is and the more light is coupled out at the light exit window. In areas close to the light source 910, e.g. in sub-area 912 of the light exit window, less outcoupling structures are present and as such less light is outcoupled at those locations. Thus, the distribution of the light outcoupling structures 964 is such that the light distribution at the light exit window is not homogeneous. This inhomogeneous light distribution at the light exit window, which converts into an inhomogeneous heat distribution in the skin, compensated for the inhomogeneous heat distribution at the light exit window resulting from the heat transfers from the light sources.

In FIG. 8 another embodiment of a flexible light therapy device 800 according to the first aspect of the invention is shown. The main body of the flexible light therapy device 800 is formed by a light transmitting element that is the combination of a flexible foam material 808 which partly encloses cavities 804 that are filled with air. The air in the cavities 804 transmits light 220 of the light sources 806 towards the light exit windows 222 of the respective cavities 804. The light exit windows 222 and the bottom side of the foam material 808 are in contact with the treatment target area 226 of the skin 224 of a person. Inside the foam material 808 heat conductive channels 802, 803 may be provided. The heat conductive channels 802, 803 may be filled by a material that is relatively flexible and conducts heat relatively well or which may be filled by a phase change material. The heat conductive channel 802 is at first locations thermally coupled to the light source 806 and at second locations thermally coupled to the heat conductive channels 803 which stretch out towards the treatment target area 226. Heat 218 of the light sources 806 is conducted via the heat conductive channels 802, 803 towards the treatment target area 226 to obtain an advantageous heat distribution at the treatment target area 226. Implementations of heat conductive channels 802 may comprise heat conductive layers, heat conductive strips or a heat conductive mesh. It is further to be noted that additional light transmitted material or structures may be provided within the cavities 804 to transmit the light from the light sources 806 to the respective light exit windows 222.

Figure 10:
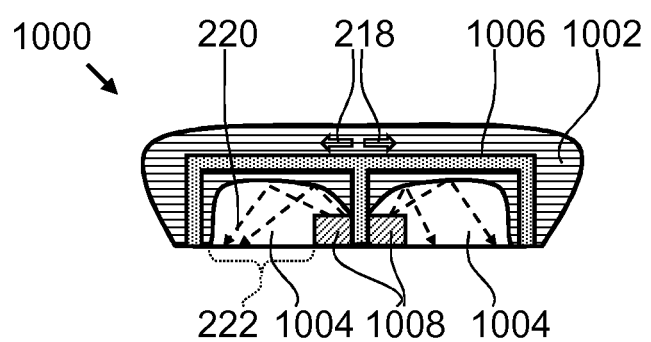

FIG. 10 shows a cross-section of another embodiment of a flexible light therapy device 1000 according to the invention. The flexible light therapy device 1000 has a flexible body 1002 which is made of a foam material. The flexible body 1002 has two cavities 1004 which are filled with air or another light transmitting medium. The flexible light therapy device 1000 further comprises two light sources 1008 which emit light 220 into the cavity and further comprises heat conductive channels 1006 which distributes heat 218 from the light sources 1008 across the treatment target area. In the cavities 1004, the foam material is provided with a reflective coating such that light 220 which impinges on the foam material is reflected towards a light exit window 222 of the cavity 1004. The shape of the cavity 1004, and thus the shape of the reflector formed by the reflective coating provided on the interface between the cavity 1004 and the flexible body 1002 is such that more light is reflected toward locations in the light exit window 222 further away from the light source. In the example of FIG. 10 the part of the light exit window close to the light sources 1008 and the ends of the heat conductive channels 1006 will be relatively warm because of the direct/indirect conduction of heat from the light sources 1008. Parts of the light exit window further away from the light source are expected to receive less heat via direct/indirect conduction, and thus it is advantageous to reflect more light 220 towards these parts of the light exit window 222. Because the more light is absorbed in the skin at locations corresponding with these further away parts of the light exit window, the skin at these locations will receive additional heat and the person who uses the flexible light therapy device 1000 experiences a more uniform temperature across the treatment target area. In the specific embodiment of FIG. 10 the part of the light exit window(s) that receives additional light than other parts, in this case by proper design of the cavity's internal surface, may be the center part of the light exit window(s). The person may not be able to differentiate between heat provided to the skin via heat conduction or via light absorption and hence 'feel' a uniform heat distribution across the treatment target area.

Figure 7A:
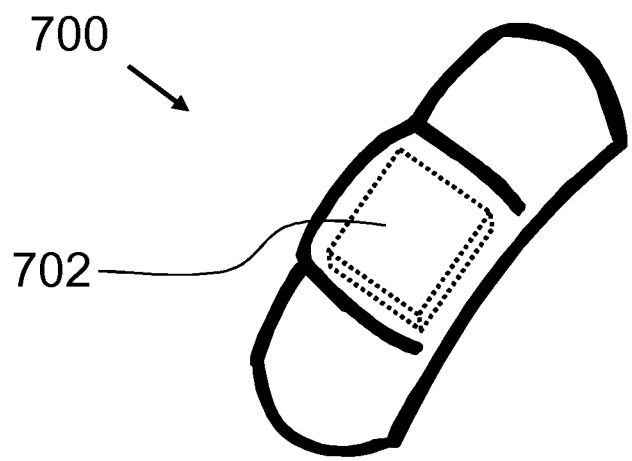
Figure 7B:
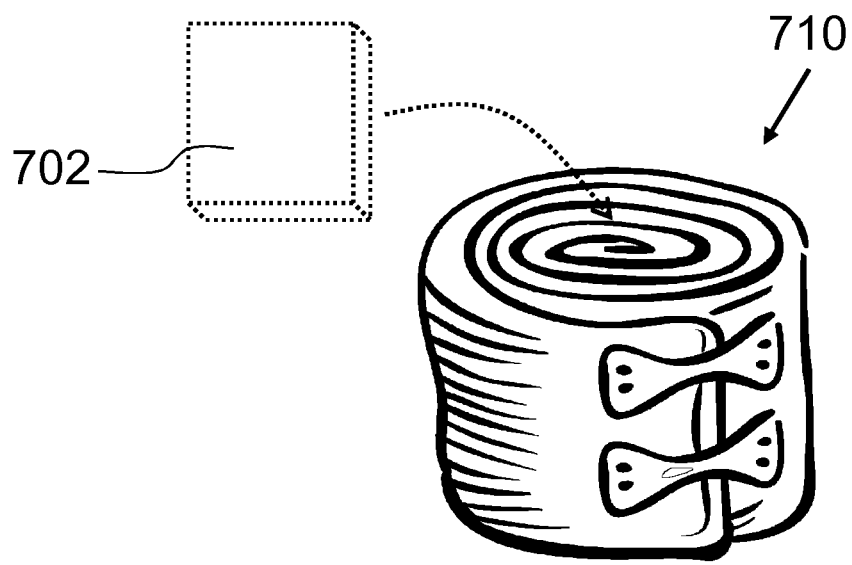

FIG. 7a schematically shows a plaster 700 which comprises the flexible light therapy device 702 according to the first aspect of the invention. In a central part of the plaster 700 is provided the flexible light therapy device 702. The light exit window of the flexible light therapy device 702 is oriented in the same direction as the adhesive surfaces of the plaster 700 which are attached to the skin of the treated person. FIG. 7b schematically shows a bandage 710 which comprises the flexible light therapy device 702 according to the first aspect of the invention.

It is to be noted that the different embodiments of a heat management means, such as for example the flexible heat spreader, or the heat conductive channels, or the fibers or the channels with the phase change material may be combined in any combination to obtain the best control of heat distribution across the light exit window. Further, different embodiments of the heat management means may be combined with different embodiment of the light transmitting element. In all embodiments an air gap may be present between light transmitting element and the treatment target area. The heat management means is not necessarily in direct thermal contact with the treatment target area but may be indirectly thermally coupled via the light transmitting element to the treatment target area.

It should be noted that the above-mentioned embodiments illustrate rather than limit the invention, and that those skilled in the art will be able to design many alternative embodiments without departing from the scope of the appended claims.

In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A flexible light therapy device for providing a therapeutic effect to a treatment area, comprising:
a light source configured to:
emit a light; and
generate a light source heat;
a flexible material, optically coupled to the light source, comprising:
a reflective or scattering portion; and
a light transmitting element comprising a light exit window
directing the light towards the treatment area; and
a heat conductive layer, comprising a phase change material for storing light source heat, thermally coupled to the light source, configured to:
receive the light source heat; and
distribute the light source heat towards the treatment area through the light transmitting element, wherein the light transmitting element and the heat conductive layer are configured to:
convey both a greater amount of said light and a lesser amount of said heat to the treatment area at a second sub-area of the light exit window than a corresponding amount of said light and a corresponding amount of said heat conveyed through the light transmitting element at a first sub-area of the light exit window, wherein the first sub-area is closer to the light source than the second sub-area and the reflective or scattering portion is at least in part arranged opposite the second sub-area.

2. The flexible light therapy device according to claim 1, wherein the heat conductive layer is thermally coupled to the light transmitting element.

3. The flexible light therapy device according to claim 1, wherein the heat conductive layer distributes the heat in time.

4. The flexible light therapy device according to claim 1, wherein the light transmitting element is shaped to provide a greater amount of the light to the second sub-area than to the first sub-area.

5. The flexible light therapy device according to claim 4, wherein the light transmitting element has a shape to control the distribution of light to the treatment area.

6. The flexible light therapy device according to claim 1, wherein said first sub-area and the second sub-area comprise the treatment area.

* * * * *